United States Patent
Goldner

(10) Patent No.: US 10,307,447 B2
(45) Date of Patent: Jun. 4, 2019

(54) FREEZE DRY PROCESS

(71) Applicant: Stephen Goldner, West Bloomfield, MI (US)

(72) Inventor: Stephen Goldner, West Bloomfield, MI (US)

( * ) Notice: Subject to any disclaimer, the term of this patent is extended or adjusted under 35 U.S.C. 154(b) by 239 days.

(21) Appl. No.: 15/451,928

(22) Filed: Mar. 7, 2017

(65) Prior Publication Data

US 2017/0252384 A1    Sep. 7, 2017

Related U.S. Application Data

(60) Provisional application No. 62/304,586, filed on Mar. 7, 2016.

(51) Int. Cl.
*A61K 36/00* (2006.01)
*A61K 36/185* (2006.01)

(52) U.S. Cl.
CPC ........ *A61K 36/185* (2013.01); *A61K 2236/17* (2013.01); *A61K 2236/37* (2013.01)

(58) Field of Classification Search
CPC .................................................... A61K 36/00
USPC ......................................................... 424/725
See application file for complete search history.

(56) References Cited

U.S. PATENT DOCUMENTS

| 8,337,908 B2 | 12/2012 | Letzel et al. |
| 8,895,078 B2 | 11/2014 | Mueller |
| 2016/0045471 A1 * | 2/2016 | Stodola ................ A61K 31/352 424/725 |
| 2018/0344663 A1 | 12/2018 | Vu et al. |

FOREIGN PATENT DOCUMENTS

CN    103289819    9/2013

OTHER PUBLICATIONS

Labconco. (2010). A guide to freeze drying for the laboratory. Labconco Corporation. Kansas City, MO. Retrieved Mar. 7, 2017 from: https://www.nbtc.cornell.edu/sites/default/files/freeze_drying_guide.pdf.

* cited by examiner

*Primary Examiner* — Michael V Meller
(74) *Attorney, Agent, or Firm* — Carlson, Gaskey & Olds, P.C.

(57) ABSTRACT

A process includes reducing one or more pieces of *cannabis* plant matter to a powder by freeze-drying the one or more pieces of *cannabis* plant matter, and then extracting one or more chemicals from the powder by pressurizing the powder in a pressure vessel with along with liquid or supercritical carbon dioxide. The carbon dioxide dissolves the one or more chemicals. The powder is then depressurized to precipitate the one or more chemicals out of the carbon dioxide, and the precipitated chemicals can then be collected. For example, the freeze-drying ruptures the plant cells in the *cannabis* plant matter, thereby exposing or releasing the chemicals in the plant cells.

2 Claims, No Drawings

FREEZE DRY PROCESS

BACKGROUND

Plant matter, such as *cannabis*, contains active chemicals that are useful for medicinal purposes to treat disease or alleviate symptoms. The active chemicals can be can be utilized in natural form in the plant matter, e.g., by smoking. Alternatively, the active chemicals can be extracted and isolated for use, for scientific study, or for other purposes. Extraction techniques, however, are inefficient. The amount of plant matter that can be processed at one time is limited, and only a small fraction of the active chemicals present are extracted.

SUMMARY

A process according an example of the present disclosure includes reducing one or more pieces of *cannabis* plant matter to a powder by freeze-drying the one or more pieces of *cannabis* plant matter, and then extracting one or more chemicals from the powder by pressurizing the powder in a pressure vessel with along with liquid or supercritical carbon dioxide. The carbon dioxide dissolves the one or more chemicals. The powder is then depressurized to precipitate the one or more chemicals out of the carbon dioxide, and the precipitated chemicals can then be collected. For example, the freeze-drying ruptures the plant cells in the *cannabis* plant matter, thereby exposing or releasing the chemicals in the plant cells.

DETAILED DESCRIPTION

The disclosed freeze dry process may enable more efficient extraction of chemicals from *cannabis* plant material. Active chemicals of interest may be extracted from *cannabis* plant matter using a solvent (e.g., carbon dioxide) extraction process. Such a process involves placement of dried *cannabis* plant matter into a pressure vessel along with liquid or supercritical carbon dioxide. Prior to extraction, *cannabis* plants can be dried naturally over time in a relatively dry environment. This natural drying may take several weeks, and yields plant matter of large piece size that may only be nominally dry.

The carbon dioxide is capable of dissolving and removing the active chemicals of interest from the dried *cannabis* plant matter. The carbon dioxide, with the dissolved chemicals, is then removed from the vessel and depressurized. Upon depressurization the chemicals precipitate from dissolution. The precipitate can then be collected and the extraction is complete. The depressurization may be conducted over several pressure intervals, at which different chemicals precipitate.

In order to extract a greater amount of the chemicals one might place a greater amount of the *cannabis* plant matter in a pressure vessel. However, using a greater amount of the dried *cannabis* plant just limits access of the carbon dioxide to the plant matter, thereby decreasing extraction efficiency. In other words, the carbon dioxide cannot contact all of the plant matter and thus cannot dissolve the active chemicals.

In the disclosed process, the *cannabis* plant matter is freeze dried. The freeze drying (or lyophilisation) reduces the piece size and also the texture of the *cannabis* plant matter that is then used in the pressure vessel. For example, *cannabis* plant matter is placed into a freeze dryer and chilled to a freezing temperature. The freezing temperature may be, but is not limited to, a temperature below about 0° C. More particularly, the selected freezing temperature may be below the triple point of water in order to ensure sublimation. The chilling can be conducted at a rapid cooling rate or a slow, controlled cooling rate. The freezing generates ice crystals. The freeze dryer can then be evacuated to a lower pressure that accelerates sublimation of the ice crystals. The *cannabis* plant matter may be held for a designated period of time at the lower pressure, to complete the sublimation to a desired degree. After freeze drying, the freeze dried *cannabis* plant matter is in a powdery form. If larger pieces remain, they are fragile and can easily be broken into fine powder form.

The powder produced from the freeze dried *cannabis* plant matter is then used in the extraction process. The powder is of substantially smaller piece (particle) size than naturally dried *cannabis* plant matter and thus has a much greater surface area (per unit weight) for exposure to the carbon dioxide in the pressure vessel. Also, the particle size of the powder may be relatively uniform. The carbon dioxide can thus more readily access and dissolve the active chemicals through the surface area (e.g., in proportion to surface area of the powder), thereby potentially increasing the percentage of active chemical that is removed from the *cannabis* plant matter in comparison to extraction of naturally dried *cannabis* plant matter. Moreover, in comparison to *cannabis* plant matter that has large piece size, a greater amount of the powder by weight (e.g., 2× or more) can potentially be used in the pressure vessel.

In a further example, unlike freeze drying that is used for preservation of tissues or other structures, the freeze drying process herein may be configured/controlled to break the plant cells in the *cannabis* plant matter. That is, the parameters of the freeze drying process, such as the freezing temperature, freezing rate, evacuation pressure, evacuation rate, or combinations thereof, can be adjusted to produce a "violent" freeze drying process that, rather than preserving microscopic structures, destroys microscopic structures via ice crystal expansion phase transformation, rapid gas evolution, and the like. Breaking the plant cells may expose or release additional amounts of chemicals and/or different chemicals that were previously non-extractable. Thus, not only can the freeze dry process be used to potentially enhance efficiency of extraction, but it can also potentially be used to access new chemicals.

The freeze dry process in combination with extraction has the potential to enable efficient collection of one or more active *cannabis*-based chemicals. Generally, the active *cannabis*-based chemicals can include one or more constituents selected from several chemical classes, including cannabinoids and terpenoids. For example, the cannabinoids can include, but are not limited to, tetrahydrocannabinol (delta-g-tetrahydrocannabinol, commonly known as "THC"), cannabidiol, cannabinol, cannabavarin, cannabigerol, cannabichromene, delta-8-THC, cannabicyclol, cannabitriol, and cannabielsoin. The terpenoids can include, but are not limited to, myrcene, limonene, and caryophyllene.

Although a combination of features is shown in the illustrated examples, not all of them need to be combined to realize the benefits of various embodiments of this disclosure. In other words, a system designed according to an embodiment of this disclosure will not necessarily include all of the features shown or described. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A process consisting essentially of:
rupturing plant cells of *cannabis* by freeze-drying the *cannabis* in order to expose or release one or more cannabinoids in the plant cells of the *cannabis*;
after rupturing the *cannabis* plant cells, extracting one or more of the cannabinoids from the *cannabis* by pressurizing the *cannabis* in a pressure vessel with along with supercritical carbon dioxide, the supercritical carbon dioxide dissolving the one or more cannabinoids, followed by depressurizing the *cannabis* in the pressure vessel, wherein the depressurizing precipitates the one or more cannabinoids out of the supercritical carbon dioxide;
isolating the one or more cannabinoids that precipitated from the supercritical carbon dioxide; and
wherein the freeze drying is performed below the triple point of water.

2. The process as recited in claim 1, wherein the depressurizing is conducted at several pressure intervals.

* * * * *